United States Patent
Ryba et al.

(10) Patent No.: US 7,163,535 B2
(45) Date of Patent: Jan. 16, 2007

(54) SYSTEM FOR DETECTING LEAKS AND OCCLUSIONS IN A CRYOABLATION CATHETER

(75) Inventors: Eric Ryba, San Diego, CA (US); Ravikumar Kudaravalli, Florence, SC (US)

(73) Assignee: Cryocor, Inc., San Diego, CA (US)

( * ) Notice: Subject to any disclaimer, the term of this patent is extended or adjusted under 35 U.S.C. 154(b) by 166 days.

(21) Appl. No.: 10/881,085

(22) Filed: Jun. 30, 2004
(Under 37 CFR 1.47)

(65) Prior Publication Data

US 2006/0004349 A1 Jan. 5, 2006

(51) Int. Cl.
*A61B 18/18* (2006.01)

(52) U.S. Cl. ............... 606/21; 606/20; 606/22; 606/23

(58) Field of Classification Search ......... 606/20–23
See application file for complete search history.

(56) References Cited

U.S. PATENT DOCUMENTS

| | | | |
|---|---|---|---|
| 3,696,813 A | 10/1972 | Wallach | |
| 3,913,581 A | 10/1975 | Ritson et al. | |
| 4,018,227 A | 4/1977 | Wallach | |
| 5,139,496 A | 8/1992 | Hed | |
| 5,281,213 A | 1/1994 | Milder et al. | |
| 5,281,215 A | 1/1994 | Milder | |
| 5,423,807 A | 6/1995 | Milder | |
| 5,697,927 A * | 12/1997 | Imran et al. ............ | 606/41 |
| 5,759,182 A | 6/1998 | Varney et al. | |
| 5,860,970 A * | 1/1999 | Goddard et al. ......... | 606/23 |
| 5,876,399 A | 3/1999 | Chia et al. | |
| 5,899,898 A | 5/1999 | Arless et al. | |
| 5,899,899 A | 5/1999 | Arless et al. | |
| 5,992,158 A | 11/1999 | Goddard et al. | |
| 6,024,740 A | 2/2000 | Lesh et al. | |
| 6,048,919 A | 4/2000 | McCullough | |
| 6,117,101 A | 9/2000 | Diederich et al. | |
| 6,139,544 A | 10/2000 | Mikus et al. | |
| 6,235,019 B1 | 5/2001 | Lehmann et al. | |
| 6,251,105 B1 | 6/2001 | Mikus et al. | |
| 6,280,439 B1 | 8/2001 | Martin et al. | |
| 6,283,959 B1 | 9/2001 | Lalonde et al. | |
| 6,383,180 B1 | 5/2002 | Lalonde et al. | |
| 6,407,149 B1 | 6/2002 | McCullough | |
| 6,440,126 B1 * | 8/2002 | Abboud et al. ......... | 606/22 |
| 6,468,268 B1 * | 10/2002 | Abboud et al. ......... | 606/20 |
| 6,471,693 B1 | 10/2002 | Carroll et al. | |
| 6,471,694 B1 * | 10/2002 | Kudaravalli et al. ..... | 606/21 |

(Continued)

*Primary Examiner*—Michael Peffley
*Assistant Examiner*—Alex Toy
(74) *Attorney, Agent, or Firm*—Nydegger & Associates

(57) ABSTRACT

A system for detecting leaks and occlusions in a cryoablation catheter requires monitoring pressure in the catheter at the end of two predetermined time intervals. The catheter includes a catheter tube, a cryo-chamber at the distal end of the catheter, and a supply line for introducing fluid refrigerant into the cryo-chamber. Also included is a pressure sensor mounted in the cryo-chamber for measuring a tip pressure. During the first time interval, fluid refrigerant is prevented from flowing through the catheter while the catheter is evacuated by a vacuum pump. The tip pressure is then measured to detect leaks. During the second time interval, fluid refrigerant is introduced into the cryo-chamber while evacuation continues, and the tip pressure is measured to detect occlusions.

20 Claims, 2 Drawing Sheets

U.S. PATENT DOCUMENTS

| | | |
|---|---|---|
| 6,527,769 B1 | 3/2003 | Langberg et al. |
| 6,540,740 B1 | 4/2003 | Lehmann et al. |
| 6,562,030 B1 | 5/2003 | Abboud et al. |
| 6,569,158 B1 * | 5/2003 | Abboud et al. ............... 606/20 |
| 6,575,966 B1 * | 6/2003 | Lane et al. .................. 606/21 |
| 6,579,287 B1 | 6/2003 | Wittenberger et al. |
| 6,585,728 B1 | 7/2003 | Heiner et al. |
| 6,585,729 B1 | 7/2003 | Eum |
| 6,589,234 B1 | 7/2003 | Lalonde et al. |
| 6,592,577 B1 | 7/2003 | Abboud et al. |
| 6,605,087 B1 | 8/2003 | Swartz et al. |
| 6,635,053 B1 | 10/2003 | Lalonde et al. |
| 6,733,494 B1 | 5/2004 | Abboud et al. |
| 6,746,445 B1 * | 6/2004 | Abboud et al. ............... 606/22 |
| 6,755,823 B1 | 6/2004 | Lalonde |
| 6,761,714 B1 | 7/2004 | Abboud et al. |
| 6,875,209 B1 * | 4/2005 | Zvuloni et al. ............... 606/21 |
| 2001/0021847 A1 | 9/2001 | Abboud et al. |
| 2001/0025075 A1 | 9/2001 | Smith et al. |
| 2002/0025998 A1 | 2/2002 | McCullough et al. |
| 2002/0026182 A1 * | 2/2002 | Joye et al. .................... 606/21 |
| 2002/0045894 A1 * | 4/2002 | Joye et al. .................... 606/21 |
| 2002/0062122 A1 | 5/2002 | Lehmann et al. |
| 2002/0111612 A1 | 8/2002 | Lalonde et al. |
| 2002/0115989 A1 * | 8/2002 | Abboud et al. ............... 606/20 |
| 2003/0004504 A1 | 1/2003 | Abboud et al. |
| 2003/0009160 A1 | 1/2003 | Carroll et al. |
| 2003/0018326 A1 | 1/2003 | Abboud et al. |
| 2003/0097124 A1 | 5/2003 | Lehmann et al. |
| 2003/0199861 A1 * | 10/2003 | Lafontaine .................. 606/21 |
| 2004/0049178 A1 | 3/2004 | Abboud et al. |
| 2004/0054361 A1 | 3/2004 | Lehmann et al. |
| 2004/0243119 A1 * | 12/2004 | Lane et al. ................... 606/21 |
| 2005/0215989 A1 * | 9/2005 | Abboud et al. ............... 606/21 |

* cited by examiner

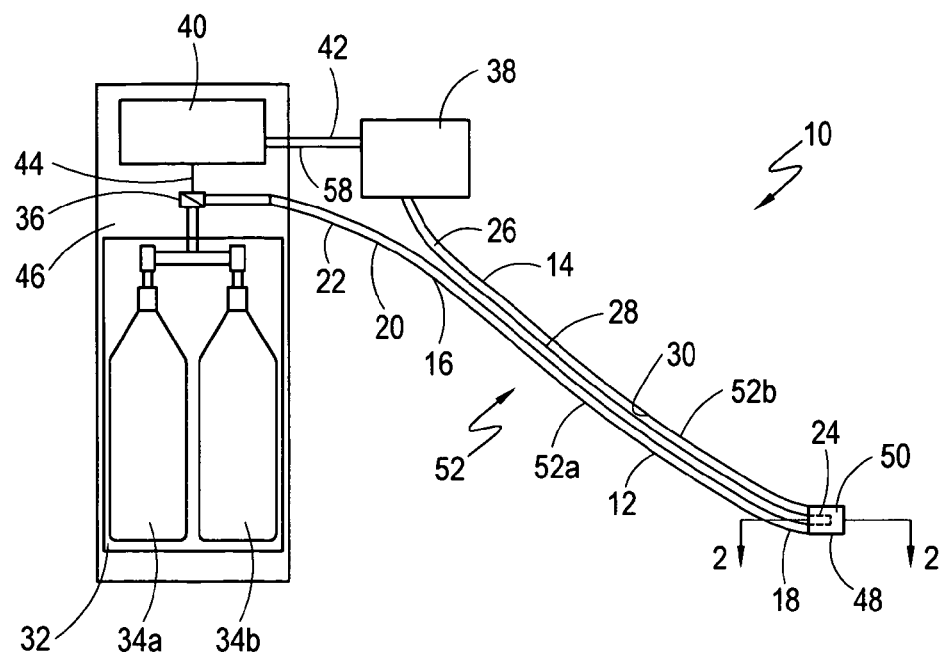
Fig. 1
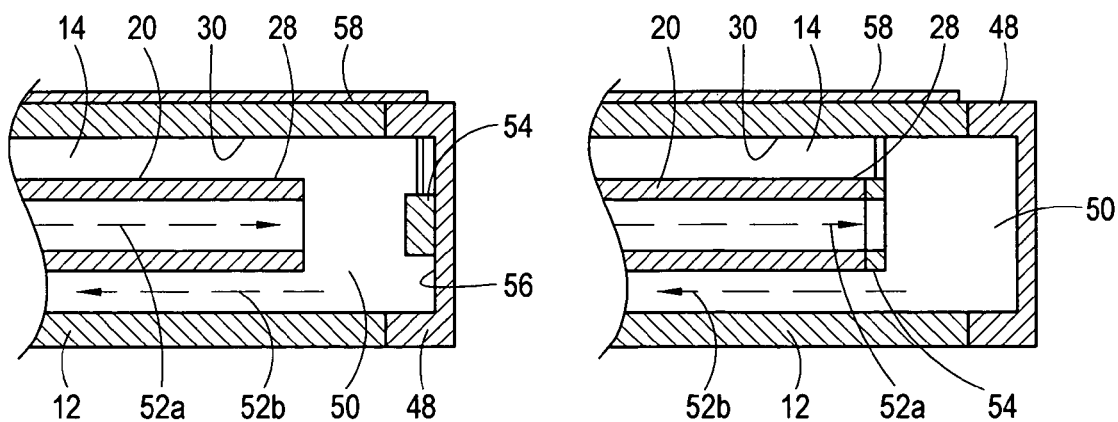
Fig. 2A
Fig. 2B

SYSTEM FOR DETECTING LEAKS AND OCCLUSIONS IN A CRYOABLATION CATHETER

FIELD OF THE INVENTION

The present invention pertains generally to catheters for surgical procedures. More particularly, the present invention pertains to systems and methods for testing the fluid integrity of surgical catheters. The present invention is particularly, but not exclusively useful as a system and method for detecting leaks and occlusions in a cryoablation catheter using pressure data measured at the tip of the cryoablation catheter.

BACKGROUND OF THE INVENTION

Cryoablation surgery is used successfully to treat certain forms of cancer, complex arrhythmias and other medical afflictions. During a cryoablation procedure, a cryo-catheter is inserted into the vasculature of a patient for cryo-ablating diseased tissue. Successful cryoablation surgery requires that the portion of the cryo-catheter in contact with the diseased tissue, referred to as the "tip", is cooled to temperatures on the order of −20° C. to −80° C. To achieve these extremely low temperatures, cryoablation systems introduce a fluid refrigerant into an expansion chamber in the tip. Functionally, the fluid refrigerant expands in the chamber. The resultant heat transfer cools the tip, and the expanded refrigerant is then exhausted from the chamber through a return line. Typically, a supply line is connected to a source of the fluid refrigerant, and is used for transferring refrigerant from the source to the expansion chamber. Further, a vacuum source is connected in fluid communication with a return line for evacuating the expanded refrigerant from the expansion chamber. For patient safety and for system efficiency, the low temperatures that are generated must be confined to the tip, and the refrigerant must be contained within an "air tight" cryo-catheter. Further, it will be appreciated that if the efficient flow of fluid refrigerant through a cryo-catheter is impeded or otherwise altered, the cryoablation catheter cannot be used effectively for its intended purpose.

Several factors may contribute to the inefficient flow of a liquid refrigerant through a cryoablating system. For example, the failure to maintain adequate flow may result from either a leak or an occlusion in the system. Under proper conditions, a leak would be indicated by a loss or reduction of the partial vacuum induced by the vacuum source. On the other hand, an occlusion would be indicated by an increased pressure at the cryo-catheter tip. In either case, i.e. a system failure resulting from either a leak or an occlusion, the system cannot achieve the required tip temperatures and the cryoablation procedure should be stopped.

During the course of a cryoablation procedure, a test for leaks and occlusions in the cryoablation system may be performed prior to inserting the catheter tube into the patient. It may be desirable, however, that the test be performed in-vivo. If so, the reliability and brevity of the test procedure are all the more critical. During an in-vivo check of the fluid integrity of a cryoablation system, a physical inspection of the components of the cryo-catheter is not possible. Therefore, the methods used to evaluate the fluid integrity of the system, in-vivo, must infer the status of the system from measured data.

For a given cryoablation catheter, the dimensions of the catheter tube are well defined (e.g. length, inner and outer diameters, volume). Also well defined (i.e. controlled) are the input pressure of the fluid refrigerant, as well as the level of partial vacuum required to evacuate the catheter tube. By knowing the dimensions of the catheter tube, the input pressure of a fluid as it is introduced into the tube, and vacuum level as fluid is being evacuated from a tube, it is possible to predict with a high degree of accuracy the consequent pressure at points within a cryoablation system. This ability to predict, however, assumes the catheter is both "air tight" and patent. Consequently, variations from predicted pressures can be indicative of a compromise in the fluid integrity of the system.

In light of the above, it is an object of the present invention to provide a system for detecting leaks and occlusions in a cryoablation catheter. Another object of the present invention is to provide a system for detecting leaks and occlusions in a cryoablation catheter wherein a tip pressure, "$p_t$", can be measured in a cryoablation chamber and used to verify the fluid integrity of the system during cryoablation surgery. Still anther object of the present invention is to provide a system for detecting leaks and occlusions in a cryoablation catheter wherein the verification of fluid integrity may be reliably and quickly performed in-vivo, without jeopardizing the health and safety of the patient. Yet another object of the present invention is to provide a system for detecting leaks and occlusions in a cryoablation catheter that is relatively easy to manufacture, is simple to use and is comparatively cost effective.

SUMMARY OF THE INVENTION

A system for detecting leaks and occlusions in a cryoablation catheter includes a catheter tube having a lumen that extends between a proximal end and a distal end of the catheter tube. Further, a supply line is coaxially positioned within the lumen of the catheter tube to form a return path between an outer wall of the supply line and an inner wall of the catheter tube. Thus, the catheter tube establishes a fluid flow path which has a first segment that extends in a downstream direction through the supply line from the proximal end of the catheter tube to the distal end of the tube. Additionally, the return path defines a second segment of the fluid flow path, which extends in a downstream direction from the distal end of the catheter tube back to the proximal end of the catheter tube.

A vacuum source is positioned at the proximal end of the catheter tube and is connected in fluid communication with the return path for evacuating the fluid flow path. Also located at the proximal end of the catheter tube is a source of fluid refrigerant for introducing pressurized fluid refrigerant into the supply line. Additionally, a supply valve connects the source of fluid refrigerant in fluid communication to the proximal end of the supply line. Functionally, the supply valve is a dual-mode valve for introducing fluid refrigerant into the supply line when the valve is in an "open" position, and for preventing the flow of fluid refrigerant into the supply line when the valve is in a "closed" position.

In addition to the fluid flow path disclosed above, the system of the present invention includes a tip member that is positioned to surround the distal end of the catheter tube to form a cryo-chamber. Mounted in the cryo-chamber is a pressure sensor for measuring a tip pressure "$p_t$". Also, a computer controller is in electronic communication with the pressure sensor for processing and evaluating pressure data received from the pressure sensor. In addition to the pressure sensor, the computer controller is in electronic communication with the supply valve for controlling the opening and closing of the valve.

In the operation of the present invention, a test for verifying the fluid integrity of a cryoablation catheter, i.e. for detecting leaks and occlusions, may be performed in-vivo or prior to inserting the catheter into the patient. Specifically, the test consists of measuring and evaluating tip pressures over the course of two well-defined time intervals, between which the fluid flow conditions of the system are varied. The measured pressure data is then compared to predetermined criteria for identifying leaks and occlusions in the system. More specifically, during the first time interval, the vacuum source is activated to evacuate the fluid flow path, and the supply valve is closed to prevent the flow of fluid refrigerant into the supply line. This first time interval is initiated at time "$t_0$", and continues to a time "$t_1$". Preferably the duration of the first time interval ($t_0$ to $t_1$) is about five seconds. At time "$t_1$", the computer controller measures a tip pressure "$p_{t_1}$". As contemplated by the present invention, if the system is "air tight" and has no leaks, the tip pressure "$p_{t_1}$" should be in the range of 2.5–3.5 psia.

In contrast with the first time interval, during the subsequent second time interval the supply valve is open and fluid refrigerant is introduced to flow through the system. Importantly, during this second time interval, the vacuum source continues to evacuate fluid refrigerant from the fluid flow path. The overall result, however, due to the introduction of fluid refrigerant, will be a measurable increase in the tip pressure in the cryo-chamber, as recorded by the computer controller. It will then happen, however, during this second time interval which extends from time "$t_1$" to a time "$t_2$", that the flow of refrigerant will be impeded if there are occlusions in the fluid flow path. To detect such a situation, at a time "$t_2$" which is preferably about five seconds after time "$t_1$", another tip pressure measurement "$p_{t_2}$" is taken by the computer controller. A measured tip pressure "$p_{t_2}$" of less than 15 psia is indicative of a patent system, wherein the fluid flow path is clear of obstructions or occlusions. At the completion of the second time interval, the test for leaks and occlusions in the system is complete, and the surgical procedure can continue. Throughout the course of the cryoablation surgery, however, the computer controller continues to monitor the pressure in the cryo-chamber, and compare the measured tip pressures to the criteria for a patent system as defined above (i.e. pressure <15 psia).

It should be understood that during either the first or the second time interval, the system may not achieve the required tip pressures (i.e. "$p_{t_1}$"=3.0 psia ±0.5 psia and "$p_{t_2}$"<15 psia). In any event, should there be a failure to achieve the required "$p_t$", the test procedure should be stopped and repeated. As soon as a tip pressure "$p_{t_1}$" of 3 psia ±0.5 psia is achieved in the first time interval, the leak detection and occlusion test is continued. Subsequently, at time "$t_2$", if the tip pressure "$p_{t_2}$" is greater than 15 psia, there is likely an occlusion in the return path and the test should be discontinued. As contemplated by the present invention, the test procedure may be repeated up to three times. After stopping the test, the cryoablation catheter can either be repaired or replaced.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a schematic view of the cryoablation system of the present invention;

FIG. 2A is a cross-sectional view of the distal end of a cryo-catheter tube, with a pressure sensor mounted on an interior surface of the tip, as would be seen along the line 2—2 in FIG. 1;

FIG. 2B is a cross-sectional view of the distal end of a cryo-catheter tube with a pressure sensor mounted on the distal end of the supply line, as would be seen along the line 2—2 in FIG. 1.

DESCRIPTION OF THE PREFERRED EMBODIMENTS

Figure 3:
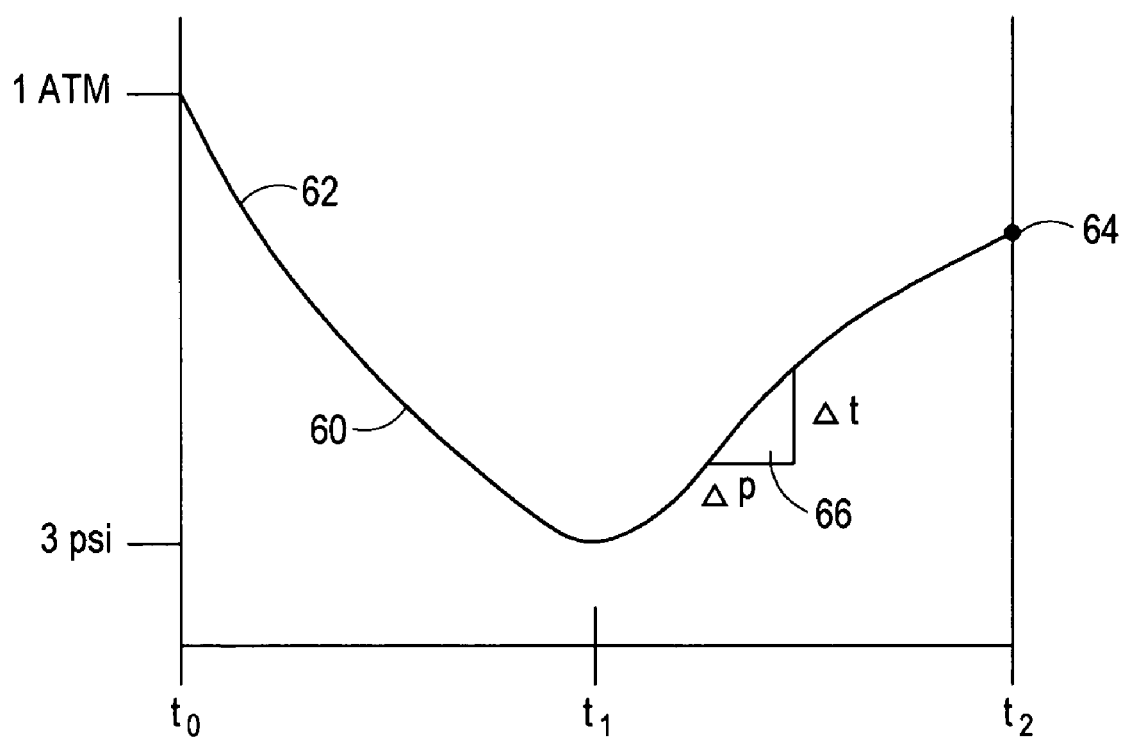
FIG. 3 is an graphical representation of a Time-Pressure curve of the present invention, plotting the tip pressure "$p_t$" as a function of time "t" during a representative test procedure.

A system for detecting leaks or occlusions in a cryoablation catheter, in accordance with the present invention, is shown in FIG. 1 and is generally designated 10. As shown, the system 10 includes a catheter tube 12 having a lumen 14 that extends from a proximal end 16 of the catheter tube 12 to a distal end 18 of the catheter tube 12. Additionally, the system 10 includes a supply line 20 having a proximal end 22 and a distal end 24. Structurally, the supply line 20 is coaxially positioned within the lumen 14 of the catheter tube 12 to form a return path 26 between an outer wall 28 of the supply line 20 and an inner wall 30 of the catheter tube 12. As shown in FIG. 1, a source of fluid refrigerant 32 is positioned at the proximal end 16 of the catheter tube 12 for introducing fluid refrigerant into the supply line 20. Preferably, the fluid refrigerant is nitrous oxide ($N_2O$). As contemplated by the present invention, the source of fluid refrigerant 32 comprises one or more storage tanks, of which tanks 34a and 34b are exemplary. It is to be understood that the tanks 34a and 34b may be any of a type of pressure vessel well known in the pertinent art that is suitable for holding, and subsequently dispensing, a fluid refrigerant under relatively high pressures (e.g. 700 psia).

Still referring to FIG. 1, a supply valve 36 is attached to the tanks 34a and 34b for connecting the source of the fluid refrigerant 32 in fluid communication with the supply line 20. As contemplated by the present invention, the supply valve 36 is a dual-mode valve, which may be either "opened" or "closed". Specifically, in the first mode the supply valve 36 is open for introducing fluid refrigerant into the supply line 20. Alternatively, in the second mode, the valve 36 is closed, thereby preventing the flow of fluid refrigerant into the catheter tube 12. As further shown in FIG. 1, a vacuum source 38 is also positioned at the proximal end 16 of the catheter tube 12 for evacuating the system 10. More particularly, the vacuum source 38 is in fluid communication with the return path 26. Further, a computer controller 40 is in electronic communication with the vacuum source 38 via an electrical cable 42. Also, the computer controller 40 is connected to the supply valve 36, via an electrical cable 44, for controlling the opening and closing of the valve 36. As shown, a console 46 houses the computer controller 40, as well as the source of the fluid refrigerant 32. As can be seen in FIG. 1, a tip member 48 is positioned to surround the distal end 18 of the catheter tube 12 to form a cryo-chamber 50.

As contemplated by the present invention, the catheter tube 12 defines a fluid flow path 52 having a first segment 52a and a second segment 52b. More specifically, the first segment 52a of the fluid flow path extends in a downstream direction from the source of the fluid refrigerant 20 to the tip member 48. Further, the second segment 52b extends in a downstream direction from the tip member 48 to the vacuum source 38. It is to be appreciated that the fluid flow path 52 defines the direction of flow of the fluid refrigerant through the system 10 during the operation of the present invention.

Referring now to FIG. 2A, the distal end 18 of the catheter tube 12 is shown in greater detail. As can be seen in FIG. 2A, a pressure sensor 54 is mounted in the cryo-chamber 50 for measuring a tip pressure "$p_t$". Preferably, the pressure sensor 54 is mounted on an inside surface 56 of the cryo-chamber 50. For the purposes of the present invention, the pressure sensor 54 may be any of a type of pressure sensors well known in the pertinent art. In an alternate embodiment of the present invention, as shown in FIG. 2B, the pressure sensor 54 is mounted on the distal end 24 of the supply line 20. As can be appreciated by referring to FIGS. 2A and 2B, an electrical wire 58 is coaxially mounted on the catheter tube 12 and connected to the pressure sensor 54. In addition, the electrical wire 58 is connected to the computer controller 40 (FIG. 1).

In the operation of the present invention, a test of the fluid integrity of the system 10 (i.e. a test for leaks and occlusions) follows a predetermined test procedure. Regardless of whether the test is performed in-vivo, or prior to inserting the catheter tube 12 into the patient, the procedures followed for the test are substantially the same. Specifically, the test consists of two well-defined time intervals during which the fluid flow conditions in the catheter tube 12 are varied. Further, tip pressure "$p_t$" measurements are taken at specified times, and the tip pressures "$p_t$" are compared to expected pressure values indicative of a catheter tube 12 free of both leaks and occlusions.

Considering now the test procedure of the present invention in detail, the system 10 is initially at ambient conditions. Stated differently, prior to initiating the test, the supply valve 36 is closed, the vacuum source 38 is turned "OFF", and the pressure in the cryo-chamber 50 is about one atmosphere. At time "$t_0$", the vacuum source 38 is activated to evacuate the fluid flow path 52, and the evacuation process continues throughout the remainder of the test procedure. During a first time interval from time "$t_0$" to time "$t_1$", which is defined as a time period of not more than five (5) seconds, there is a drop in tip pressure "$p_t$". Referring now to FIG. 3, it can be seen that the tip pressure "$p_t$" decreases from time "$t_0$" to time "$t_1$". More specifically, in the region 60 of the Time-Pressure curve 62, between time "$t_0$" and time "$t_1$", it can be seen that the tip pressure "$p_t$" decreases from about one atmosphere to about 3 psia. At time "$t_1$", a tip pressure "$p_{t_1}$" measurement is taken by the computer controller 40. Importantly, the tip pressure "$p_{t_1}$" should be in the range of 3.0 psia ±0.5 psia (i.e. 2.5–3.5 psia). If the tip pressure "$p_{t_1}$" is 3.0 ±0.5 psia, as shown in FIG. 3, the test is continued.

Following the first time interval, the supply valve 36 is opened and fluid refrigerant is introduced into the supply line 20. As envisioned by the present invention, the fluid refrigerant flows through the supply line 20 (the first segment 52a of the fluid flow path 52) and into the cryo-chamber 50. In the cryo-chamber 50, the fluid refrigerant cools the tip member 48, and is subsequently evacuated via the return path 26 (i.e. the second segment 52b of the fluid flow path 52). During this second time interval, from time "$t_1$" to a time "$t_2$", the pressure in the cryo-chamber 50, as measured by the pressure sensor 54, increases. As will be appreciated by the skilled artisan, the pressure sensor 54 may be of any type well known in the pertinent art, such as a pressure tap tube (not shown). As contemplated by the present invention, at the end of the second time interval, a tip pressure "$p_{t_2}$" measurement is taken at a time "$t_2$". Preferably, time "$t_2$" is not more than five (5) seconds after time "$t_1$". In any event, the tip pressure "$p_{t_2}$" should be less than 15 psia. Accordingly, if the tip pressure "$p_{t_2}$" is less than 15 psia, as represented by point 64 in FIG. 3, the test procedure is complete. In addition to the tip pressure measurement "$p_{t_2}$", an important aspect of the present invention is the rate of change in pressure ("$\Delta p/\Delta t$") from time "$t_1$" to time "$t_2$". During the time interval from "$t_1$" to "$t_2$", a very rapid rise in pressure toward a pressure of 15 psia is a first indication of an occlusion in the return path 26. If the $\Delta p/\Delta t$ exceeds the expected rate of increase, the system should be activated to stop the test. Alternatively, if the tip pressure "$p_{t_2}$" is less than 15 psia, and the rate of change in pressure ($\Delta p/\Delta t$ 66 in FIG. 3) is equal to an acceptable value for the system 10, the return path 26 is considered to be occlusion free and the cryoablation procedure may proceed.

It should be understood that during either the first time interval ("$t_0$"–"$t_1$") or the second time interval ("$t_1$"–"$t_2$"), the system may not achieve the required tip pressures "$p_t$". In the event the required pressures are not achieved, the test should be stopped and repeated as appropriate. If the required tip pressure "$p_t$" is still not achieved, the cryo-catheter should be inspected and replaced as necessary. For example, during the first time interval, if the tip pressure "$p_{t_1}$" is not 3 psia ±0.5 psia, the test procedure should be stopped and repeated. After stopping the test, the system 10 is returned to its initial configuration, which is to say the vacuum source 38 is turned "OFF" and the system 10 returns to ambient conditions. Importantly, the test procedure may be repeated up to three times. If the system 10 achieves a tip pressure "$p_{t_1}$" of 3 psia ±0.5 psia during any one of the three attempts, the leak detection and occlusion test is continued. If the system 10 fails to achieve the required tip pressure at time "$t_1$", however, the procedure is stopped and the cryoablation catheter is inspected and replaced, if necessary. It can be appreciated by the skilled artisan that the most likely reasons for the system 10 not achieving the desired tip pressure "$p_{t_1}$" are: (1) an improper fluid connection between the catheter tube 12 and the vacuum source 38; (2) a loose connection between the computer controller 40 and the electrical wire 58 connected to the pressure sensor 54; or, (3) a compromise of the fluid integrity of the catheter tube 12. One or all three of these potential causes must be inspected, and repaired as necessary, before the leak and occlusion test can proceed. Also, if at time "$t_2$" the tip pressure "$p_{t_2}$" is greater than 15 psia, there is likely an occlusion in the return path 26 and the test is discontinued. After stopping the test, the cryoablation catheter is either repaired or replaced.

While the particular System for Detecting Leaks and Occlusions in a Cryoablation Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for detecting leaks and occlusions in a cryoablation catheter which comprises:

a catheter tube defining a lumen, said catheter tube having a proximal end and a distal end;
a tip member attached to said distal end of said catheter tube to surround said distal end thereof to form a cryo-chamber;
a supply line coaxially positioned in said lumen of said catheter tube to define a return path between said supply line and said catheter tube, wherein said supply line has a distal end and a proximal end, with said distal end of said supply line positioned in said cryo-chamber;
a source of fluid refrigerant;
a supply valve for connecting said source of fluid refrigerant in fluid communication with said supply line for selectively introducing fluid refrigerant into said supply line when said supply valve is in an open position, and for preventing the flow of fluid refrigerant into said supply line when said supply valve is in a closed position;
a vacuum source in fluid communication with said return path;
a means for detecting leaks in the system by measuring a tip pressure "$p_t$" in said cryo-chamber when said vacuum source is activated during a first time interval when said supply valve is in a closed position; and
a means for detecting occlusions in the system by measuring the tip pressure "$p_t$" during a second time interval when said supply valve is in an open position.

2. A system as recited in claim 1 wherein said means for detecting occlusions in the system includes a means for monitoring a rate of change in tip pressure "$p_t$".

3. A system as recited in claim 1 wherein the first time interval is between a time "$t_0$" and a time "$t_1$", and further wherein a tip pressure "$p_{t_1}$" is measured at time "$t_1$", the tip pressure "$p_{t_1}$" being indicative of an air-tight system when the tip pressure "$p_{t_1}$" is in the range of 2.5 to 3.5 psia.

4. A system as recited in claim 3 wherein the second time interval is between time "$t_1$" and a time "$t_2$", and further wherein a tip pressure "$p_{t_2}$" is measured at time "$t_2$", the tip pressure "$p_{t_2}$" being indicative of a patent system when the tip pressure "$p_{t_2}$" is less than 15 psia.

5. A system as recited in claim 4 which further comprises a computer controller in electronic communication with said detecting means and said supply valve for establishing the first time interval and the second time interval and for respectively evaluating "$p_{t_1}$" and "$p_{t_2}$".

6. A system as recited in claim 5 wherein the first time interval and the second time interval are each about 5 seconds in duration.

7. A system as recited in claim 1 wherein said fluid refrigerant is nitrous oxide.

8. A system for detecting leaks and occlusions in a catheter which comprises:
a catheter tube having a proximal end and a distal end, and defining a fluid flow path, wherein said fluid flow path has a first segment extending in a downstream direction from said proximal end of said catheter tube to said distal end of said catheter tube and a second segment extending in a downstream direction from said distal end of said catheter tube to said proximal end of said catheter tube;
a fluid source;
a supply valve for connecting in fluid communication said fluid source with said first segment of said fluid flow path at said proximal end of said catheter tube, for selectively introducing fluid into said first segment when said supply valve is in an open position, and for preventing the flow of fluid into said first segment when said supply valve is in a closed position;
a vacuum source connected in fluid communication with said second segment of said fluid flow path at said proximal end of said catheter tube for evacuating said fluid flow path;
a means for detecting leaks in the system by measuring a pressure "$p_t$" when said vacuum source is activated during a first time interval when said supply valve is in a closed position; and
a means for detecting occlusions in the system by measuring the tip pressure "$p_t$" during a second time interval when said supply valve is in an open position.

9. A system as recited in claim 8 wherein the first time interval is between a time "$t_0$" and a time "$t_1$", and further wherein a pressure "$p_{t_1}$" is measured at time "$t_1$", the pressure "$p_{t_1}$" being indicative of an air-tight system when the pressure "$p_{t_1}$" is in the range of 2.5 to 3.5 psia.

10. A system as recited in claim 9 wherein the second time interval is between time "$t_1$" and a time "$t_2$", and further wherein a pressure "$p_{t_2}$" is measured at time "$t_2$", the pressure "$p_{t_2}$" being indicative of a patent system when the pressure "$p_{t_2}$" is less than 15 psia.

11. A system as recited in claim 10 wherein the first time interval and the second time interval are each about 5 seconds in duration.

12. A system as recited in claim 10 which further comprises a computer controller in electronic communication with said detecting means and said supply valve for establishing the first time interval and the second time interval and for respectively evaluating "$p_{t_1}$" and "$p_{t_2}$".

13. A system as recited in claim 8 wherein said fluid is a refrigerant.

14. A system as recited in claim 13 wherein said fluid refrigerant is nitrous oxide.

15. A method for evaluating the fluid integrity of a cryoablation catheter having a proximal end and a distal end, the method comprising the steps of:
connecting a source of fluid refrigerant to said proximal end of said cryoablation catheter for selectively introducing fluid refrigerant into said cryoablation catheter, wherein said cryoablation catheter defines a fluid flow path having a first segment and a second segment, and further wherein said first segment is connected to said source of fluid refrigerant and extends in a downstream direction from said source of fluid refrigerant to said distal end of said cryoablation catheter;
activating a vacuum source positioned at said proximal end of said cryoablation catheter, wherein said vacuum source is in fluid communication with said second segment of said fluid flow path for evacuating said fluid flow path, and further wherein said second segment extends in a downstream direction from said distal end of said cryoablation catheter to said vacuum source;
measuring a pressure "$p_{t_1}$" at an intersection of said first segment and said second segment of said fluid flow path during a first time interval;
introducing a fluid refrigerant into said first segment of said fluid flow path during a subsequent second time interval;
measuring a pressure "$p_{t_2}$" at an intersection of said first segment and said second segment of said fluid flow path during the second time interval;
monitoring a rate of change in pressure at the intersection of said first segment and said second segment of said fluid flow path during the second time interval; and comparing the pressure measurements "$p_{t_1}$" and "$p_{t_2}$" respectively to known values and comparing the rate of change in pressure to a known value for evaluating the fluid integrity of said cryoablation catheter.

16. A method as recited in claim 15 wherein the first time interval is between a time "$t_0$" and a time "$t_1$", and further wherein a pressure "$p_{t_1}$" is measured at time "$t_1$", the pressure "$p_{t_1}$" being indicative of an air-tight cryoablation catheter when the pressure "$p_{t_1}$" is in the range of 2.5 to 3.5 psia.

17. A method as recited in claim 16 wherein the second time interval is between time "$t_1$" and a time "$t_2$", and further wherein a pressure "$p_{t_2}$" is measured at time "$t_2$", the pressure "$p_{t_2}$" being indicative of a patent cryoablation catheter when the pressure "$p_{t_2}$" is less than 15 psia.

18. A method as recited in claim 17 wherein the first time interval and the second time interval are each about 5 seconds in duration.

19. A method as recited in claim 17 which further comprises the step of operating a computer controller for establishing the first time interval and the second time interval and for respectively evaluating "$p_{t_1}$" and "$p_{t_2}$".

20. A method as recited in claim 15 wherein said fluid refrigerant is nitrous oxide.

\* \* \* \* \*